United States Patent [19]

Baudet

[11] 4,443,613

[45] Apr. 17, 1984

[54] IMINO-ALKYL AND AMINO-NITRILE CYANO-GUANIDINE

[76] Inventor: Pierre J. Baudet, 15 ch. Passoret, Geneva 1227, Switzerland

[21] Appl. No.: 428,748

[22] Filed: Sep. 30, 1982

Related U.S. Application Data

[62] Division of Ser. No. 197,985, Oct. 14, 1980, Pat. No. 4,383,115.

[30] Foreign Application Priority Data

Feb. 14, 1979 [CH] Switzerland .................... 1404/79

[51] Int. Cl.$^3$ ............................................ C07D 233/64
[52] U.S. Cl. .................................................. 548/342
[58] Field of Search ......................................... 548/342

[56] References Cited

U.S. PATENT DOCUMENTS 4,093,621  6/1978  Brown et al. ............... 548/342 X

*Primary Examiner*—Richard A. Schwartz
*Attorney, Agent, or Firm*—Pennie & Edmonds

[57] ABSTRACT

The invention relates to cyanoguanidine derivatives characterized by an imino-alkyl and amino-nitrile structure having the general formula:

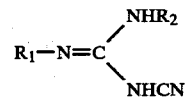

in which $R_1$ is a 2-mercapto-ethyl, 2-hydroxy-ethyl, a 2-((4-methyl-5-imidazoly)thio-methyl)ethyl, or a 2-((4-methyl-5-imidazolyl)dithioformyloxy-methyl)ethyl radical, and $R_2$ is the methyl radical. The invention relates to the manufacture of imino-methyl and amino-nitrile cyano-guanidines.

One compound of invention: N-methyl-N'-cyano-N''-imino-[2-((4-methyl-5-imidazolyl)thio-methyl) ethyl] guanidine is a histamine antagonist in the $H_2$ receptors and inhibits the secretion of gastric acid. It can be used thereapeutically for the treatment of gastric and duodenal ulcers.

1 Claim, No Drawings

IMINO-ALKYL AND AMINO-NITRILE CYANO-GUANIDINE

This is a division of application Ser. No. 197,985 filed Oct. 14, 1980, now U.S. Pat. No. 4,383,115.

TECHNICAL FIELD

This invention relates to a novel group of cyanoguanidine derivatives characterized by the following imino-alkyl and amino-nitrile structural formula:

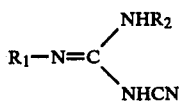
IV wherein $R_1$ is a 2-mercapto-ethyl, a 2-hydroxy-ethyl, a 2-((4-methyl-5-imidazolyl)thio-methyl)ethyl, or a 2-((4-methyl-5-imidazolyl)dithioformyloxy-methyl)ethyl radical, and $R_2$ represents a methyl radical.

A particularly advantageous compound of the invention: N-methyl-N'-cyano-N''-imino-[2-((4-methyl-5-imidazolyl)thio-methyl) ethyl] guanidine is a histamine antagonist in the $H_2$ receptors which inhibits the secretion of gastric acid, and can be used therapeutically for the treatment of gastric and duodenal ulcers.

This invention also relates to processes for the production of these novel cyanoguanidine derivatives.

BACKGROUND OF THE INVENTION

Cyanoguanidine derivatives synthesized by known processes are characterized by imino-nitrile guanidine structures having the following formula:

II

The stable conformations of the cyanoguanidines of formula II are represented by the following structures:

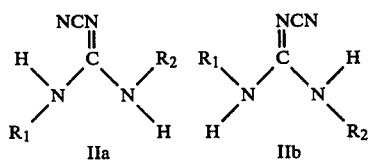

Structures IIa and IIb represent the anti(—$NHR_2$) and syn(—$NHR_2$) geometrical isomers of the formula II cyanoguanidines. These isomers do not demonstrate the phenomenon of tautomery and thus, are not intermediates for the production of amino-nitrile and imino-alkyl cyanoguanidines having the following formula:

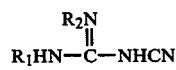
I

In solution, the IIa and IIb isomers do not transform into each other. A high energy barrier prevents establishment of either a tautomeric or an E to Z isomeric equilibrium. This high energy barrier results from the rapidity of inversion of the —NCN group (probably by a rotational-bond mechanism) which is greater than the rate of rotation of the —$NHR_1$ and —$NHR_2$ groups.

SUMMARY OF THE INVENTION

This invention discloses a group of cyanoguanidine derivatives characterized by the following imino-alkyl and amino-nitrile formula:

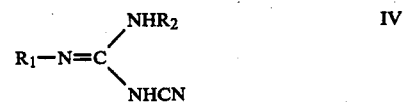
IV wherein $R_1$ and $R_2$ may or may not be identical. The invention also relates to a method for producing these novel cyanoguanidines.

Cyanoguanidines conforming to structure IV are unique, and their intermediate guanidines of structure I do not represent tautomers of either of the known formula II cyanoguanidines. The phenomenon of tautomery involves the establishment of an equilibrium between the tautomers. If the formula I and II cyanoguanidines were in fact tautomers, upon dissolving the formula II cyanoguanidine in a suitable solvent, the corresponding formula I cyanoguanidine would also be found in the solution. It may be hypothesized that the absence of the formula I cyanoguanidine is due to an equilibrium situation in which the quantity of the formula I cyanoguanidine is reduced to a level at which its presence cannot be detected. If this were the case however, upon dissolving a formula I cyanoguanidine in the same solvent, it would be expected that it would be transformed into the corresponding formula II cyanoguanidine until it no longer existed in the solution above a trace amount. This does not occur, and it has been established that:

(1) in solutions of formula II cyanoguanidines, the presence of the corresponding formula I cyanoguanidine is not detected;

(2) in solutions of formula I cyanoguanidines, the presence of the corresponding formula II cyanoguanidine is not detected.

DETAILED DESCRIPTION OF THE INVENTION

Stable conformations which can be isolated from the formula I cyanoguanidines are the following:

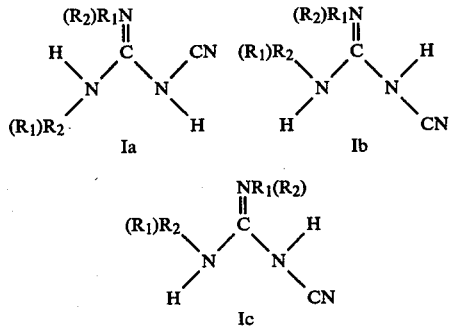

The absence of a demonstrated tautomery phenomenon between the formula Ia, Ib, Ic cyanoguanidines and the formula IIa or IIb cyanoguanidines is due to the respective molecular stability of each of these cyanoguanidine groups. The molecular stability of formula Ia and Ib cyanoguanidines is, most likely, caused by an interaction of the amino-nitrile component with the imino-alkyl component; within a planar structure. This interaction leads to a considerable decrease in the electrical moment of the nitrile component, as reflected by the disappearance of its infra-red absorption. The molecular stability of the formula Ia and Ib cyanoguanidines is also attributed to the basicity of the imino-alkyl and the amino-nitrile guanidine functional groups, allowing the formation of, for example, stable salts such as a hydrochloride of the particular guanidine. This interaction, and the effected molecular stability are no longer manifested when, for example, a formula I cyanoguanidine is dissolved in acetonitrile or dimethylformamide at temperatures between about 50° and 80° C. and, consequently, infra-red absorption is demonstrated by the amino-nitrile component. The disappearance of the molecular stability characteristic leads to the establishment of an equilibrium with new tautomers. This phenomenon can be effected using the hydrochloride of the chosen guanidine, but it appears more rapidly when the corresponding base of the guanidine is used. Neutralization of the hydrochloride by an equivalent quantity of alkaline alkoxide permits development of the infra-red absorption described above. The established equilibrium can be depicted as follows:

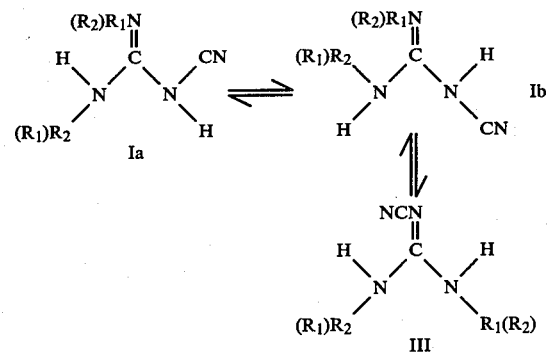

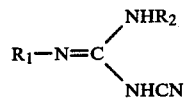

As demonstrated above, it is seen that compounds having the Ia or Ib formulas are tautomers of formula III compounds (imino-nitrile tautomers demonstrating less stability.)

The rapidity of inversion of the $C=NR_1(R_2)$ group of formula Ia and Ib structures is less than that of the rotation of the $-NHR_2(R_1)$ and $-NHCN$ groups. This represents an opposite phenomenon to that observed with formula IIa and IIb cyanoguanidines. This difference in dynamic behavior is the reason why the Ia and Ib cyanoguanidines demonstrate tautomery, while formula IIa and IIb cyanoguanidines do not.

For these reasons, formula I cyanoguanidines cannot be obtained from formula II cyanoguanidines by a displacement of equilibrium. Instead, the existence of formula I cyanoguanidines depends upon: (1) the invention of a reactant which will provide, stereospecifically, the desired configuration or (2) the discovery of a reaction characterized by the irreversible displacement of the double bond of the guanidine functional group.

According to this invention, a guanidine derivative of the following formula, is provided:

$$R_1-N=C\underset{NHCN}{\overset{NHR_2}{\diagup}} \qquad IV$$

which is characterized by an imino-alkyl and amino-nitrile components and wherein $R_1$ is a 2-mercapto-ethyl, a 2-hydroxy-ethyl, 2-((4-methyl-5-imidazolyl)thio-methyl) ethyl, or a 2-((4-methyl-5-imidazolyl)dithioformyloxymethyl)ethyl radical, and $R_2$ represents a methyl radical.

The compounds of the invention are:
N-methyl-N'-cyano-N''-imino-(2-mercapto-ethyl) guanidine, N-methyl-N'-cyano-N''-imino-(2-hydroxy-ethyl) guanidine, N-methyl-N'-cyano-N''-imino-[2-((4-methyl-5-imidazolyl)-thio-methyl) ethyl] guanidine, N-methyl-N'-cyano-N''-imino-[2-((4-methyl-5-imidazolyl)-di-thioformyl-oxymethyl) ethyl] guanidine.

The process for the preparation of the cyanoguanidine compounds of this invention includes the irreversible transformation of formula II cyanoguanidines into formula I cyanoguanidines by means of an intermediate HX reactant, in which X represents $Cl^-$, $Br^-$, $I^-$, $PO_4H_2^-$, $SO_4H^-$, $4CH_3C_6H_4SO_3^-$. The elimination of HX leads to the novel amino-nitrile and imino-alkyl structure of formula I cyanoguanidines:

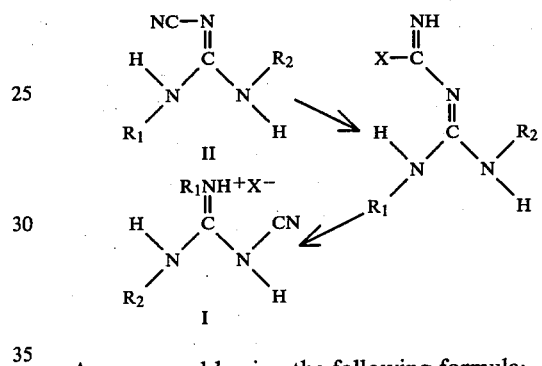

A compound having the following formula:

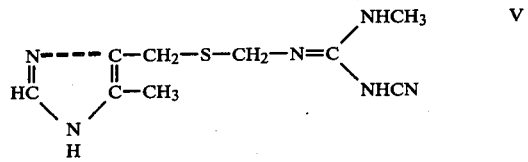

may be prepared according to any of the following processes:

(1) condensing a reactant which already possesses the desired tautomery form, N-methyl-N'-cyano-N''-imino (2-mercapto-ethyl)guanidine, for example, with 4-methyl-5-chloromethyl-imidazole. or, (2) condensing a sodium or potassium xanthogenate of N-methyl-N'-cyano-N''-imino(2-hydroxy-ethyl)-guanidine with 4-methyl-5-chloromethyl-imidazole and subjecting the obtained xanthate to a Chugaev-type transformation. or, (3) reacting a compound having the following formula:

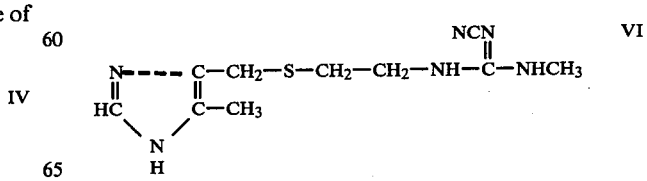

with a hydrogenated mineral, such as HCl for example, to give an addition intermediary, from which the mineral is then eliminated, to yield, for example, a dihydrochloride of the formula V compound.

Formula V compounds, as well as the therapeutically suitable salts of these compounds, antagonize the activity of histamine in the $H_2$ receptors, thus blocking the histamine's stimulation of hydrochloric acid production in the stomach. Formula V compounds are also advantageously used for the therapeutic treatment of gastric and duodenal ulcers. Suitable excipients for pharmaceutical forms of formula V compounds are, for example, lactose, saccharose, talcum, gelatine, arabic gum or olive oil.

EXAMPLES

The following examples are set forth for the purpose of illustration only and are not to be construed as limiting the scope of the invention in any manner.

EXAMPLE 1

Preparation of N-methyl-N'-cyano-N''-imino-(2-mercapto-ethyl) guanidine 0.76 g of HCl in ether is added to a solution of 2.42 g of N-methyl-N'-cyano-N''-imino-(2-tetrahydropyranylthio-ethyl) guanidine in dry ethanol. After a reaction time of 40 minutes, infra-red spectrophotometry indicates the absence of absorptions by the nitrile component and the presence of absorption activity by the addition intermediary. The intermediary is precipitated by an ether and the imino-(2-mercapto-ethyl)guanidine is crystallized as hydrochloride by rubbing. The imino-(2-mercapto-ethyl)guanidine is then transformed in water by $AgNO_3$ into the Ag mercaptide derivative of N-methyl-N'-cyano-N''-imino (2-mercapto-ethyl)guanidine as hydrochloride. The following are observed:

| | |
|---|---|
| Chloride ion titration | 99.5% |
| IR (film): | 1710, 1655 |
| (cm$^{-1}$) | 1590, 1455, 1380, 1300 |

EXAMPLE 2

Preparation of N-methyl-N'-cyano-N''-imino-(2-hydroxy-ethyl)guanidine as hydrochloride Two equivalents of HCl in dry ether are added to a solution of 4.26 g of N-methyl-N'-cyano-imino-N''-(2-hydroxy-ethyl)guanidine in dry methanol. After 30 minutes, there is no infra-red absorption by the nitrile component and the IR absorptions of the addition intermediary are as follows: 1670, 1630, 1580, 1565 (cm$^{-1}$). The intermediary is precipitated by an ether and the resulting oil is taken up by methanol. The hydrochloride of N-methyl-N'-cyano-N''-imino-(2-hydroxy-ethyl)guanidine is crystallized out by rubbing, m.p. 184°–186° C. The following are observed:

| $C_5H_{10}N_4O.HCl$ (178.5) | | | |
|---|---|---|---|
| | % C | % H | % N |
| Calculated | 33.61 | 5.60 | 31.37 |
| Found | 33.43 | 5.72 | 31.25 |
| IR (nujol) | 3250, 3120, 1720 (doublet), | | |
| (cm$^{-1}$) | 1665, 1600 (doublet), 1510, 1400, 1290, | | |
| | 1260, 1105, 995, 950, 900, | | |
| | 850 (doublet), 700. | | |

EXAMPLE 3(a)

Preparation of N-methyl-N'-cyano-N''-imino[2-((4-methyl-5-imidazolyl) thio-methyl)ethyl]guanidine as dihydrochloride 3 equivalent parts of HCl in ether are added to a solution of 2.52 g of N-methyl-N'-imino-cyano-N''-2-((4-methyl-5-imidazolyl)ethyl guanidine in dry ethanol. After 30 minutes, IR absorption activity of the nitrile component disappears, and IR absorption activity of the addition intermediary is apparent (1665, 1630, 1570 cm$^{-1}$.) The intermediary is precipitated with ether and the resulting oil is washed by the ether and taken up by methanol, from which, by rubbing, the dihydrochloride of the N-methyl-N'-cyano-N''imino[2-((4-methyl-5-imidazolyl) thio-methyl)ethyl]guanidine is crystallized; m.p. 120°–122° C. The following are observed:

| | |
|---|---|
| IR (nujol) | 3300, 3200, 3100, 2700, 2650, 1700, |
| (cm$^{-1}$) | 1665, 1590, 1410, 1400, 1360, 1315, |
| | 1290, 1260, 1245, 1210, 1165 (doublet), |
| | 1100, 1025, 935, 870, 780, 700 |

EXAMPLE 3(b)

Preparation of N-methyl-N'-cyano-N''-imino-[2-((4-methyl-5-imidazolyl) thio-methyl)ethyl]guanidine as monohydrochloride The dihydrochloride of N-methyl-N'-cyano-N''-imino-[2-((4-methyl-5-imidazolyl)thio-methyl)ethyl]-guanidine as prepared in Ex. 3(a), is mixed with a molar excess of triethylamine. A small amount of methanol is added to the mixture in order to dissolve it completely. After 20 minutes, the solvent is evaporated under reduced pressure and the monohydrochloride of N-methyl-N'-cyano-N''-imino-[2-((4-methyl-5-imidazolyl)thiomethyl)ethyl]guanidine is crystallized in acetonitrile; m.p. 174°–176° C.

The following results are recorded:

| $C_{10}H_{16}N_6S.HCl$ (288.5) | | | | |
|---|---|---|---|---|
| | % C | % H | % N | % S |
| Calculated | 41.59 | 5.85 | 29.11 | 11.09 |
| Found | 41.46 | 5.95 | 29.04 | 11.12 |
| IR (nujol) | 3200, 3080, 1710, 1644, 1605, 1570, | | | |
| (cm$^{-1}$) | 1480, 1395, 1340, 1305, 1230, | | | |
| | 1150 (doublet), 1080, 1065, 1040, 1010, 1005, | | | |
| | 960, 845, 780 (doublet), 690, 660 | | | |

EXAMPLE 4

Preparation of N-methyl-N'-cyano-N''-imino[2-((4-methyl-5-imidazolyl)thio-methyl)ethyl]guanidine as monohydrochloride 0.68 g of sodium hydride and 8 ml of carbon disulfide are added to a suspension of 1.80 g of N-methyl-N'-cyano-N''-imino-(2-hydroxy-ethyl) guanidine as hydrochloride in dry tetrahydrofuran. After a reaction time of 15 hours, 1.52 g of 4-methyl-5-chloro-methylimidazole in dry ethanol is introduced into the medium under agitation. The mixture is taken to reflux and carbon oxysulfide is liberated. After the solvent is evaporated, the residue is neutralized with an equivalent part of HCl and crystallized in acetonitrile as a monohydrochloride with a m.p. 174°–176° C.

EXAMPLE 5

Preparation of N-methyl-N'-cyano-N''-imino [2-((4-methyl-5-imidazolyl)thio-methyl)ethyl] guanidine as monohydrochloride 1.95 g of N-methyl-N'-cyano-N''-imino-(2-mercapto-ethyl) guanidine, as hydrochloride, followed by 1.95 g of sodium ethoxide are added to a solution of 1.30 g of 4-methyl-5-chloromethyl-imidazole in dry ethanol, under inert gas such as argon. After a reaction time of 5 hours, the NaCl is separated by filtration and the product is isolated by evaporation of the solvent. The monohydrochloride is crystallized after neutralization by an equivalent part of HCl in acetonitrile. F. 174°–176°.

EXAMPLE 6

Preparation of N-methyl-N'-cyano'-N''-imino [-2((4-methyl-5-imidazolyl)thio-methyl)-ethyl] guanidine as dihydrochloride 1.95 g of hydrochloride of N-methyl-N'-cyano-N''-imino-(2-mercapto-ethyl) guanidine is added to a solution of 1.90 g of hydrochloride of 4-methyl-5-acetoxy-methyl-imidazole in dry ethanol. The mixture is refluxed for 12 hours. The dihydrochloride product is crystallized out in methanol, m.p. 120°–122° C.

EXAMPLE 7

Preparation of N-methyl-N'-imino-cyano-N''-[2-((4-methyl-5-imidazolyl)thio-methyl)-ethyl] guanidine The monohydrochloride of N-methyl-N'-cyano-N''-imino-2-((4-methyl-5-imidazolyl)thio-methyl)ethyl guanidine is refluxed for 16 hours in acetonitrile containing a small amount of methanol. After neutralization, the base is isolated as an oil. The following are observed:

| IR (film) (cm$^{-1}$) | 3200, 3100, 2150, 1580–1560, 1475, 1440, 1390, 1285, 1225, 1170, 1080, 790 |
|---|---|

EXAMPLE 8

Preparation of N-methyl-N'-cyano-imino-N''[-2-((4-methyl-5-imidazolyl)thio-methyl)-ethyl] guanidine 3.2 g of the monohydrochloride or 3.6 g of the dihydrochloride of N-methyl-N'-cyano-N''-imino-2-((4-methyl-5-imidazolyl)thio-methyl)ethyl guanidine is neutralized in ethanol. The NaCl is separated by filtration, the solvent is evaporated and the residue is taken up with dimethylformamide. This solution is maintained at 62° for 7 hours. The solvent is then evaporated under 0.02 T.

The residue is extracted with acetonitrile and after evaporation under reduced pressure, an oil is obtained. The following are observed:

| IR (film) (cm$^{-1}$) | 3200, 3100, 2150, 1580–1560, 1475, 1440 1390, 1285, 1170, 1080, 790 |
|---|---|

What I claim is:
1. A cyanoguanidine having the structural formula:

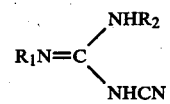

characterized by the imino-alkyl and amino-nitrile structure wherein $R_1$ comprises a 2-((4-methyl-5-imidazolyl)dithioformyloxy-methyl)ethyl radical and $R_2$ comprises a methyl radical.